United States Patent [19]

Gustafson et al.

[11] Patent Number: 4,707,361

[45] Date of Patent: Nov. 17, 1987

[54] GRANULAR ANHYDROUS DICALCIUM PHOSPHATE COMPOSITIONS SUITABLE FOR DIRECT COMPRESSION TABLETING

[75] Inventors: Carl G. Gustafson, Peekskill; Carolyn A. Ertell, Yonkers, both of N.Y.

[73] Assignee: Stauffer Chemical Company, Westport, Conn.

[21] Appl. No.: 761,988

[22] Filed: Aug. 2, 1985

[51] Int. Cl.[4] .................. C01B 15/16; C01B 25/26; A61K 33/06; A61K 7/16

[52] U.S. Cl. .................. 424/154; 423/307; 423/308; 424/57; 424/128; 424/474; 514/835

[58] Field of Search .............. 424/14, 57, 128, 154; 423/307, 308; 514/835

[56] References Cited

U.S. PATENT DOCUMENTS

| | | | |
|---|---|---|---|
| Re. 29,077 | 12/1976 | Geller | 424/15 |
| 2,018,410 | 10/1935 | McDonald et al. | 424/57 |
| 2,196,150 | 4/1940 | Heald | 424/57 |
| 2,943,982 | 7/1960 | Dahlin | 424/57 |
| 3,068,067 | 12/1962 | Aia | 423/308 |
| 3,095,269 | 6/1963 | Chiola et al. | 423/308 |
| 3,134,719 | 5/1964 | Sheth et al. | 167/82 |
| 3,208,821 | 9/1965 | Lehr et al. | 23/109 |
| 3,210,154 | 10/1965 | Klein et al. | 23/106 |
| 3,334,979 | 8/1967 | Saunders et al. | 423/313 |
| 3,353,908 | 11/1967 | Cremer et al. | 423/159 |
| 3,784,708 | 1/1974 | Ranucci et al. | 424/357 |
| 3,829,562 | 8/1974 | Kim et al. | 424/57 |
| 4,036,928 | 7/1977 | Valenta | 264/115 |
| 4,044,105 | 8/1977 | Enomoto et al. | 423/308 |
| 4,048,337 | 9/1977 | Fabbian | 424/357 |
| 4,115,307 | 9/1978 | McGilvery | 252/135 |
| 4,154,799 | 5/1979 | Hauge | 423/308 |
| 4,187,803 | 2/1980 | Valenta | 119/1 |
| 4,193,973 | 3/1980 | Jarvis et al. | 423/308 |
| 4,244,931 | 1/1981 | Jarvis et al. | 423/308 |
| 4,247,526 | 1/1981 | Jarvis et al. | 423/308 |
| 4,472,365 | 9/1984 | Michel | 423/308 |
| 4,487,749 | 12/1984 | Sherif et al. | 423/308 |
| 4,496,527 | 1/1985 | Sherif et al. | 423/308 |
| 4,524,054 | 6/1985 | George et al. | 423/308 |

FOREIGN PATENT DOCUMENTS

| | | |
|---|---|---|
| B249637 | of 1966 | Austria . |
| 0054333 | 6/1982 | European Pat. Off. . |
| 0124027 | 11/1984 | European Pat. Off. . |
| 0127400 | 12/1984 | European Pat. Off. . |
| 59-223206 | 12/1984 | Japan ............ 424/57 |
| 59-223208 | 12/1984 | Japan ............ 424/57 |
| WO81/02521 | 9/1981 | PCT Int'l Appl. . |

OTHER PUBLICATIONS

John R. Van Wazer, *Phosphorus and Its Compounds*, vol. 1: Chemistry, Interscience Publishers, Inc., New York, N.Y., 1958, pp. 521, 522, 1646 and 1651.
Chem. Abstracts, 95:67921f, (1981).
Chem. Abstracts, 79:111315g, (1973).
Chem. Abstracts, 92:203506s.
Kirk–Othmer Encyclopedia of Chem. Tech., 3rd Ed., vol. 17, p. 446, (also p. 445).
Chem. Abstracts, 94, 90250z, (1981).
Chem. Abstracts, 95:12650m, (1981).

*Primary Examiner*—Ronald W. Griffin
*Attorney, Agent, or Firm*—Paul J. Juettner

[57] ABSTRACT

A granular anhydrous dicalcium phosphate having a particle of a size sufficient for direct compression tablets and a surface area of greater than 5 meters$^2$/gram can be direct compression tableted. This product can be prepared by dehydrating granules of dicalcium phosphate dihydrate of a particle size sufficient for direct compression tableting and sufficiently large to allow the dehydration of the granules without lumping and without fracturing a majority of the granules. The granules are heated at a temperature sufficient to form anhydrous dicalcium phosphate. The product is a granular anhydrous dicalcium phosphate exhibiting good compressibility, flowability and whiteness while being in an anhydrous state.

27 Claims, No Drawings

GRANULAR ANHYDROUS DICALCIUM PHOSPHATE COMPOSITIONS SUITABLE FOR DIRECT COMPRESSION TABLETING

The present invention relates to granular anhydrous dicalcium phosphate compositions which are suitable for direct compression tableting and to tablets produced by direct compression.

BACKGROUND OF THE INVENTION

In compressing a dry particulate material into tablets, the direct compression technique is the most desirable. It employs the fewest steps and, in the case of pharmaceutical tablets containing sensitive or unstable active materials, minimizes the contact of the active ingredient with water, organic solvents or other conditions tending to adversely effect the stability thereof.

Tableting material for dry direct compression must be compressible into a tablet form, and must produce strong tablets with good tablet surfaces and good strength, particularly under the stress of automatic tableting equipment. The direct compression vehicle must be flowable into the dies of high speed tableting machines without bridging as so often occurs with fine powders. Since the amount of active material contained in a tablet is based on the weight of the tablet, weight variations caused by improper flow cannot be tolerated. The vehicle must also have good stability under normal ambient conditions so that it can be effectively compressed.

Most powdered dry materials are impractical for direct compression tableting, particularly in automatic tableting equipment because of compressive strength and/or flow problems. Some of these powders can be granulated using a wet granulation process, with or without the addition of an adhesive substance. The moistened powder is converted into a crumbly mass which is forced through a screen to reduce the material to a grain-like structure of small granules. It is then dried, milled and sieved.

The powder can also be dry granulated by precompressing the dry powder, such as, into slugs or passing the material between two compressing rollers followed by breaking the material into granular particles of uniform size.

Granular tricalcium phosphate, also known as granular tribasic calcium phosphate, and unmilled dicalcium phosphate dihydrate, also known as unmilled dibasic calcium phosphate dihydrate, are effective direct compression vehicles.

Anhydrous dicalcium phosphate, which has also been used in tableting, has generally been prepared by precipitating the product from a slurry of lime and phosphoric acid which has been heated above 80° C. (see U.S. Pat. No. 3,095,269). U.S. Pat. No. 3,334,979 discloses a precipitated anhydrous dicalcium phosphate which is a hard abrasive material having a dentin abrasion (Radioactive Dentin Abrasivity) value of about 200 (see note on page 4). Precipitated anhydrous dicalcium phosphate is a fine, dense powder which must be agglomerated with a binder such as starch before it can be used in direct compression tableting.

Anhydrous dicalcium phosphate can also be prepared by driving off the water of hydration at moderately elevated temperature or on storage. The presence of free moisture accelerates dehydration, though a hard mass can be obtained (Kirk-Othmer, Encyclopedia of Chemical Technology, 3$^{rd}$ Edition, Vol. 17, page 446). U.S. Pat. No. 3,095,269 discloses the preparation of anhydrous dicalcium phosphate by boiling a slurry of DCPD at a pH below 5.5. At pH's near 5.5, cubic crystals of a size smaller than the diamond shaped crystals achieved at lower pH's are obtained. U.S. Pat. No. 3,095,269 further teaches that there is a problem in controlling the drying rate to effect gradual release of large quantities of chemically bound water. Excessive rate of drying tends to cause degradation of well-formed crystals due to sudden release of the water. This results in excessive break-up or fracture of the dihydrate particles, formation of fines and wide particle size distribution. U.S. Pat. No. 3,334,979 discloses that the dentin abrasion value of a dehydrated dicalcium orthophosphate dihydrate is about 60 (see Note on page 4).

Anhydrous dicalcium phosphate can also be prepared by precipitation from a mother liquor containing a combination of monoammonium phosphate with ammonium and calcium chloride (U.S. Pat. No. 3,068,067). Anhydrous dicalcium phosphate can also be prepared from a monoalkali metal phosphate solution in combination with gypsum in a mill (U.S. Pat. No. 3,353,908).

These anhydrous dicalcium phosphates alone cannot be used in dry direct compression as the particles are too fine and will not flow into the compression dies. These compounds cannot meet U.S. Pharmacopia (U.S.P.) standards without further treatment as they contain ammonium, chloride or sulfate ions. These anhydrous compositions cannot be dry granulated to make a dry direct compression tableting composition.

SUMMARY OF THE INVENTION

In accordance with the present invention there is provided a granular anhydrous dicalcium phosphate which can be direct compression tableted characterized by a particle size sufficient to be used in direct compression tableting, a dentin abrasion value of less than about 150 and a surface area greater than 5 meters$^2$/gram. The product is a "soft" granular anhydrous dicalcium phosphate which is a direct compression vehicle exhibiting good compressibility, flowability and whiteness while being in an anhydrous state.

This new product can be prepared by dehydrating granules of dicalcium phosphate dihydrate of a particle size sufficient to be usable in direct compression tableting at a temperature and under conditions sufficient to produce anhydrous dicalcium phosphate without forming lumps or fractured particles. Preferably, heating is conducted at a temperature and for a time sufficient to reduce the Loss on Ignition (L.O.I.) at 800° C. to an amount ranging from about 11 percent to about 6.6 percent by weight.

DETAILED DESCRIPTION OF THE INVENTION

The anhydrous dicalcium phosphate of the invention has particles of a size sufficient to be used in direct compression tableting. Compositions which are too fine or which contain a significant amount of fines lack the flowability needed to form tablets of uniform weight and thickness in a tableting machine. Preferably the particles are above 44 microns and at least 80 percent above 74 microns. The particles can contain fines in amounts insufficient to retard flowability into the tableting dies. Preferably less than 10 percent and more preferably less than 5 percent of the particles are less than 44 microns. The upper limit on particle size is that size which can be processed in a tabletting machine. Preferably, particle size is less than about 840 microns (20 mesh) and more preferably less than 5 percent greater than 420 microns (40 mesh) for flowability into the tabletting machine.

The product of the invention is an anhydrous dicalcium phosphate which can be characterized as "soft" in its abrasiveness. By "soft" is meant having a "dentin abrasion value" or Radioactive Dentin Abrasivity (RDA) values of below about 150 and preferably below about 100. The abrasiveness of the anhydrous dicalcium phosphate was determined by the procedure set forth in the Journal of Dental Research, Volume 55, Number 4, 1976, p. 563; wherein "dentin abrasion values" are assigned after a dentifrice composition has been utilized in the mechanical brushing of radioactive dentin from extracted human teeth. The roots of previously extracted teeth are made radioactive and are brushed for a standard number of strokes at a standard pressure using a slurry containing the abrasive material. The radioactive phosphorus 32 removed from the dentin is used as an index of abrasion. A standard using calcium pyrophosphate is arbitrarily assigned a value of 100. The dentin abrasion values presently used are one-fifth that of the values in the original test. The standard calcium pyrophosphate, which was originally assigned an arbitrary abrasion value of 500, has been reassigned a value of 100. As used herein, all dentin abrasion values, even those in reference material, have been normalized to the later standard.

The surface area of the anhydrous product is greater than about 5 meters$^2$/gram and preferably greater than about 7 and more preferably greater than about 9 meters$^2$/gram as determined by the BET nitrogen absorption method. The upper limit of surface area is dictated by practical considerations of product manufacture.

The product of the invention can be prepared by processes which allow the dehydration of dicalcium phosphate dihydrate while providing the necessary particle size, surface area and softness. The dicalcium phosphate dihydrate can be prepared by any method which provides granules of a size effectively large for tabletting, preferably having at least 90 percent above 44 microns (325 mesh), and more preferably at least 80 percent above 74 microns (200 mesh). The upper limit on particle size is that size which can be processed in a tabletting machine. Preferably, particle sizes less than about 840 microns (20 mesh) and more preferably less than 5 percent greater than 420 microns (40 mesh) are used.

The granules can be formed as a result of the manufacturing process of the dicalcium phosphate dihydrate, or milled and/or agglomerated to the proper size or by compaction and comminution. Any methods which can form the proper granule size are envisioned as useful though the two methods subsequently described are preferred.

One of the preferred methods is the compaction and comminution method. In this method, the conversion of particles of dicalcium phosphate dihydrate to granules useful in the invention is carried out in two steps, compaction and comminution.

The dihydrate can be compacted by the static application of force such as by using an hydraulic press. Preferably, the dihydrate is compressed by feeding a densified powder mass of the dihydrate under controlled volume flow into the nip of the counterrotating rolls of a roller compactor. The roller compactor can be of the type sold under the trademark CHILSONATOR as described in U.S. Pat. No. 3,255,285.

The compaction step can be carried out at a high or low rate of application of pressure. In an hydraulic press the rate of application of force can range from about 325 kilograms (716 pounds) to about 700 kilograms (1543 pounds) per second. In a roller compactor the force employed for the compaction step can vary from about 714 kilograms force/linear centimeter roll width (4,000 pounds/linear inch) to about 3214 kilograms force/linear centimeter roll width (18,000 pounds/linear inch) or higher. The preferred range in applied force for compaction is from about 1428 kilograms force/linear centimeter roll width (8,000 pounds/linear inch) to about 2,500 kilograms force/linear centimeter roll width (14,000 pounds) in the aforementioned roller compactor.

The thickness of the compacted material in the case of the hydraulic press is determined by the amount of powder charged. In the case of the roller compactor, the thickness of the ribbon produced is determined by the rate of feed of powder into the nip between the rolls, as well as the configuration of the rolls and the force applied to the rolls.

The particle size of the fine powder used as the feed material varies from about 0.5 micron to about 75 microns with a majority of the particles being within the range of from about 25 to about 75 microns. The bulk density of the fine particle feed to the compacting process of the present invention ranges from about 0.15 to about 0.5 g/cc (10–30 lbs/ft$^3$).

The surface of the rolls or plates applying the mechanical force can be scored to give corrugated, patterned or briquetted compacted product of any desired shape. Corrugations facilitate the flow of the fine feed into the nip of the rolls.

Compaction can be carried out at low relative humidity and ambient temperature. The compaction step in exerting mechanical pressure on the fine particles of the calcium phosphate by means of rolls increases the temperature about 10° C. to about 30° C. Chilling the pressure rolls is unnecessary unless discoloration of the compacted material commences.

The compacted product is then comminuted by any means appropriate to produce the particle sizes which can effectively be dehydrated in accordance with the invention, such as by grinding.

Grinding mills such as those manufactured by the Fitzpatrick Company, Elmhurst, Ill.; Pulverizing Machinery Company, Summit, N.J.; and Raymond Division of Combustion Engineering Company, Stamford, Conn., can be used to prepare the desired sized granules from the compacted sheet, ribbon, flakes or chips.

Optionally, the compacted ribbon or sheet of the blend can be pre-broken up into flakes, chips, slices or pieces by standard cutting machines prior to grinding. It is convenient to attach a rotating set of cutting knives just below the compacting chamber of a continuous roller compactor so that the ribbon of compacted material is immediately broken up into pieces varying in size from about 5 millimeters to 50 millimeters. The speed of rotation of the prebreaking knives varies from about 40 to about 1000 rpm, thus determining the size of the pieces.

After comminuting, the product is classified to provide the desirable particle size for a direct compression vehicle. Any appropriate screening or sieving device including screens, perforated plates, cloth and the like, and air separators and the like can be used if appropriate classification of particles can be obtained.

Following classification, the particles having the desired particle size range are segregated for further processing. The fine and large particles can be recycled to the compactor for further processing.

The granular dicalcium phosphate dihydrate (normal L.O.I. of about 25 percent) is then dehydrated by heating to a temperature and for a time sufficient to reduce the L.O.I. below about 11 percent. Any further weight loss below the L.O.I. of 6.6 percent occurs by formation of pyrophosphate. Preferably, the L.O.I. is reduced to a range of from about 6.6 percent to about 8.5 percent, the range given in U.S. Pharmacopia for anhydrous dicalcium phosphate. 6.6 percent is the calculated lower L.O.I. limit for anhydrous dicalcium phosphate.

Dehydration can be initiated at about 75° C. Temperatures of above about 90° C. are preferred for higher rates of dehydration. Temperatures above 300° C. are not desirable as they may lead to pyrophosphate formation. The type of equipment may contribute to the temperature range utilized.

The granules are heated for a period of time sufficient to form the desired L.O.I. Times can vary depending on the temperature and equipment used. These conditions are easily determined by one of ordinary skill in the art.

The granules of dicalcium phosphate dihydrate for dehydration by the previously discussed process can also be isolated directly from the manufacturing process therefor by any process which provides granules in the desired range without milling. A suggested process for preparing such granules includes the following steps:
1. reacting a slaked lime slurry with phosphoric acid to form a monocalcium phosphate solution;
2. adding to the solution additional amounts of the slaked lime slurry as well as a stabilizing amount of a pyrophosphate, to form a dicalcium phosphate dihydrate slurry having a pH ranging from about 4.9 to about 5.5, temperatures in steps 1 and 2 not to exceed about 40° C.;
3. separating the dicalcium phosphate dihydrate from the slurry, drying the separated dicalcium phosphate dihydrate; and
4. separating fine particles from coarse particles.

Steps 1, 2 and 3 are more specifically disclosed in U.S. Pat. No. 4,312,843, the disclosure of which is incorporated herein by reference. Drying in step 3 can be accomplished using any convenient drying means that does not destroy the dihydrate. Particle size classification can be accomplished by sieves, screens, air separators and the like. Particle classification can be accomplished before or after dehydration.

The unmilled dicalcium phosphate dihydrate is separated in order to provide a final product having substantially all particles effectively usable in direct compression tableting, for example preferably 90 percent and above greater than 44 microns (325 mesh), and more preferably about 80 percent greater than 74 microns (200 mesh). The unmilled dicalcium phosphate dihydrate preferably has less than 1 percent particles greater than 840 micron particle size (20 mesh) and less than 5 percent greater than 420 micron particle size (40 mesh). While larger particles can be milled to desirable size, milling can affect compactability by removing surface characteristics from the particles which contribute to adhesion. If milling is required, it is preferred that particles larger than 840 microns (20 mesh) are separated first and then milled.

After dehydration, fines (for example, smaller than 44 microns) produced by fracturing can be included in the product if not excessive (below 10 percent) or separated by particle classification means such as those discussed above. It is also within the scope of the invention to dehydrate dicalcium phosphate dihydrate of a broad particle size range and classify particles after dehydration.

It has also been found that a pH adjusting agent can be added to provide a final pH different from the native pH. Examples of such pH adjusting agents include tetrasodium pyrophosphate (TSPP). The pH adjusting agent can be added to the phosphate at any time before tableting, i.e. before, during or after compaction.

The products of the invention can be made into tablets by direct compression using well-known techniques. Prior to tableting, the active ingredient(s) along with other ingredients such as binders, disintegrants, colorants, flavors, diluents and any other materials normally used in tablets can be blended with the granules. A lubricant is usually blended last to coat the surface of the particles and provide exterior lubrication.

After mixing, the blend can be formed into a tablet by dry, direct compression. Either single hydraulic units or multiple anvil high-speed rotary tableting units can be used as known in the industry. The tablets can be formed in any desired shape such as round tablets or dry capsules with equivalent results. The composition of the present invention can be compressed at a high rate of compression in a rotary tableting machine as well as a low rate of compression utilizing a single tablet hydraulic unit with effective results.

The product of the invention can also be used as a filler in capsules or as an absorbent for oily material such as fragrances. The product of the invention is anhydrous dicalcium phosphate and can be used as such as is known in the art.

The invention is illustrated in the Examples which follow. All percentages and ratios are by weight unless otherwise stated.

EXAMPLE I

USP/FCC grade of dicalcium phosphate dihydrate, manufactured by Stauffer Chemical Company, was compacted in a Fitzpatrick Chilsonator ™ system provided with rolls of 10 centimeters (4 inches) in width and 25 centimeters (10 inches) in diameter. The rolls had a sine-wave surface and were separated with a roll gap of 0.05 centimeter (0.020 inches). The powder mixture was fed to the Chilsonator compactor by a vertical-screen type conveyor and compacted by the rolls. One roll was hydraulically forced against the other with a pressure of 70 kg/sq centimeter gauge (2200 psig). The roll force was about 2143 kilograms per linear centimeter (12,000 pounds per linear inch). The rolls had a rotational speed of 16 rpm.

The compacted sheet product was directly charged to a Fitzmill ™ (Model DASO6) mill equipped with rotating knife-blades. The product was discharged from the mill through a screen which had round openings of 0.125 centimeter (0.05 inch).

The compacted and milled product was directly fed onto a vibrating screening unit. The screens used were 120 centimeters (48 inches) in diameter. The first screen was rated at 36 TBC (tensile bolting cloth). The second screen was rated at 78 TBC. These vibrating screens separated the feed into three portions. The product cut was taken from the middle portion, i.e., particles that passed the 36 TBC screen but could not pass the 78 TBC screen. The oversize and undersize fractions that came out of the vibrating screens were discharged into the Chilsonator feed hopper, blended with the raw feed for the Chilsonator compactor and recycled.

A sieving analysis performed on the product showed there was no particles coarser than 20 mesh and that a majority of the product had particle sizes between 20 and 60 mesh (U.S. Standard Sieve Series).

The compacted dicalcium phosphate dihydrate was blended with a pyrophosphate stabilizer in a V-blender for 20 minutes without an intensifier bar and dehydrated in a 50 centimeter rotary dryer having an outer cylinder closed on one end with a diameter of about 50 centimeters and a depth of about 55 centimeters and an inner cylinder closed on one end with a diameter of about 40 centimeters and a depth of about 60 centimeters. Motive power means were attached to the closed end. The dryer was elevated 15° from the horizontal. A gas flame was positioned to direct heat into the inner cylinder. A thermocouple for measuring temperature was placed inside the dryer.

The compacted and granulated dicalcium phosphate dihydrate was heated to effect dehydration. During the initial heating, the temperature rose to a point between about 90° C. and 100° C. in about 10 minutes where the temperature was maintained for about 10 minutes and most of the water was lost. Heating was continued for approximately an additional 30-40 minutes after the sample reached about 150° C. The product with an L.O.I. of between about 7.9 percent and 8.2 percent was discharged into a stainless steel container to be cooled.

The product was subjected to three quality control tests, i.e. particle size distribution, L.O.I. at 800° C. and pH for a 20 percent solid slurry. In the sievings, only a trace of material remained on 40 mesh. The particles had a surface area of about 9.8 meters$^2$/gram. The following results were obtained:

TABLE I

| Ex. No. | TSPP Parts Per 100 parts DCPD | pH | L.O.I. % |
|---|---|---|---|
| 1 | 0 | 5.73 | 7.94 |
| 2 | 1.0* | 6.51 | 7.92 |
| 3 | 0.25 | 6.09 | 7.99 |
| 4 | 0.5 | 6.19 | 7.90 |
| 5 | 1.5 | 7.02 | 7.88 |
| 6 | 1.0 | 6.86 | 7.96 |

| | Sieving | | | |
|---|---|---|---|---|
| Ex. No. | 40/60 | 60/80 | 80/100 | −100 |
| 1 | 46 | 41 | 10 | 3 |
| 2 | 46 | 40 | 10 | 4 |
| 3 | 45 | 41 | 11 | 4 |
| 4 | 48 | 40 | 9 | 3 |
| 5 | 46 | 40 | 10 | 4 |
| 6 | 48 | 39 | 9 | 4 |

*TSPP not V-blended - slow dried

Tablets were prepared by placing the anhydrous and 0.5 percent magnesium stearate lubricant in a twin shell V-blender (Patterson-Kelley) equipped with an intensifier bar. The mixture was blended for 2 minutes with the intensifier bar off.

The formulations were formed into tablets by dry direct compression on a rotary tableting machine (Manesty B3B) equipped with 7/16 inch IPT standard cup tooling. The tableting machine was equipped with strain gauges attached to a recorder to record the compression force applied to each tablet run. Four stations out of a possible 16 tableting stations on the machine were used. Tablets were produced at a rate of 750 tablets per minute based on 16 stations. Nominal tablet weight was 750 milligrams.

The tablets were tested for hardness using a Schleuniger Tablet Hardness Tester, Model 2E/106. Hardness is reported as an average of the hardness of 10 tablets.

The percentages are weight percent. All tablet formulations contain 0.5 percent lubricant. The lubricant was magnesium stearate. The following results were obtained:

TABLE II

| | TABLE DATA | |
|---|---|---|
| Experiment No. | Tablet Weight Variation Coefficient Cv @ 20 kN - % | Hardness (Kiloponds) Average of 10 Tablets |
| 1 | .5 | 18 |
| 2 | .3 | 20 |
| 3 | .5 | 17 |
| 4 | .2 | 19 |
| 5 | .2 | 19 |
| 6 | .2 | 19 |

The tablet weight variation coefficient or percent tablet weight variation was used to determine flow. Generally a value of less than 1 percent indicated good flow.

EXAMPLE II

USP/FCC grade of dicalcium phosphate dihydrate, manufactured by Stauffer Chemical Company, was used in this Example with or without a preliminary blending with a pyrophosphate stabilizer. If the pyrophosphate was used, the dihydrate was charged into a V-blender along with the pyrophosphate and was blended for about 20 minutes.

The above-identified blended powder, or the dihydrate itself if no pyrophosphate was preblended, was then compacted in a Fitzpatrick Chilsonator system, as generally described in Example 1, Model 1.5L×8D (rolls of 1.5 inches in length and 8 inches in diameter—3.81 centimeters×20.32 centimeters).

The compacted product was in the form of broken sheets or small sticks. The compacted product was directly charged to a Fitzmill Homoloid Machine (Model JT) equipped with rotating knife blades. The mill was operated at a speed of 750-800 rpm. The product was discharged directly from the mill through a screen whose size is identified in the Table hereinafter.

The compacted and milled product was then fed to a Sweco Vibro-Energy Separator Unit. The unit was 45 centimeters (18 inches) in diameter and had a top screen of 38 TBC (tensile bolting cloth) mesh size 0.0495 centimeter (0.0198 inch) and a bottom screen of 84 TBC mesh size 0.021 centimeter (0.0084 inch). The middle cut that went through the top screen but was retained on the bottom screen was fed to a second Sweco Vibro-Energy Separation Unit. This second unit was equipped with a single 60 mesh screen (0.023 centimeter or 0.0092 inch openings). The product cut that was retained on the 60 mesh screen was taken as the intermediate material to be dehydrated.

If the pyrophosphate was added after compaction, it was done at this stage by blending the compacted material and a food-grade anhydrous pyrophosphate powder in a Patterson-Kelley 0.15 cubic meter (5 cubic feet) twin-shell blender. A 20 minute blending time was used to insure a uniform mixture.

The dehydration was carried out as described in Example I. The temperature of the material was elevated and a rapid dehydration reaction took place and water escaped as steam at approximately 80°-100° C. Heating was continued to 150° C. and the drying process took approximately 60 minutes to complete. The product was naturally cooled in a closed-top stainless steel vessel.

The product was observed to be a white, granular material which appeared to flow well. Its pH was determined on a 20 percent slurry in water. The product had a surface area of about 13.1 meters$^2$/gram. Its L.O.I. was determined by heating the material in an 800° C. oven for 20 minutes. The material was also classified with a RO-TAP Testing Sieve Shaker, Model B, for 10 minutes. Tablets were prepared as in Example I. The results are reported in TABLE III hereinafter.

TABLE III

| Ex. No. | TSPP* | pH | L.O.I. |
|---|---|---|---|
| 1 | 0.5 | 6.56 | 8.19 |
| 2** | 0.5 | 6.56 | (8.19) |
| 3 | 1.0 | 6.50 | 8.06 |
| 4*** | 1.0 | 6.47 | 8.11 |
| 5 | 0 | 5.94 | 8.06 |

| | Sieving Analysis | | | | |
|---|---|---|---|---|---|
| Ex. No. | +40 | 40/60 | 60/80 | 80/100 | −100 |
| 1 | 7 | 32 | 24 | 15 | 22 |
| 2** | 9 | 53 | 32 | 4 | 1 |
| 3 | 14 | 54 | 26 | 3 | 3 |
| 4*** | 14 | 51 | 28 | 3 | 3 |
| 5 | 8 | 56 | 33 | 2 | 1 |

*Parts/100 parts calcium phosphate
**Resieving of Experiment 1
***Second sample of Experiment 3

Tablets were made of the product according to the procedure set forth in Example I with the following results:

TABLE IV

TABLET DATA

| Experiment No. | Tablet Weight Variation Coefficient Cv @ 20 kN - % | Hardness (Kiloponds) Average of 10 Tablets |
|---|---|---|
| 1 | 2.3 | 19 |
| 2 | 0.3 | 12 |
| 3 | 0.7 | 18 |
| 4 | 0.4 | 18 |
| 5 | 0.3 | 16 |

EXAMPLE III

Milled USP/FCC grade dicalcium phosphate dihydrate with a majority of particle sizes less than 25 microns was treated according to the procedure of Example II with the exception that 0.75 part per hundred pyrophosphate stabilizer was used and in one experiment the pyrophosphate was added before drying but after compaction.

Because of the initial small particle size, these experiments were not successful.

EXAMPLE IV

Unmilled dicalcium phosphate dihydrate having a particle size of about 64.4 percent on 100 mesh, 31.9 percent through 100 mesh and on 200 mesh and less than 1 percent through 325 mesh, manufactured by Stauffer Chemical Company, and sold under the trademark DI-TAB®, was dehydrated in a convection oven.

Two aluminum trays containing 3.2 kilograms (7 pounds) of the dicalcium phosphate dihydrate were placed in the oven and dehydration was effected by heating. Heating was continued for sufficient time to reduce loss on ignition from 24-26 percent to 8-9 percent.

The product was subjected to three quality control tests, i.e. particle size distribution, L.O.I. at 800° C. and pH for a 20 percent solids slurry. The product of Experiment 2 had a surface area of about 14.4 meters$^2$/gram. The following results were obtained:

TABLE V

| Ex. No. | Dehydration Temp. °C. | Time Hr. | pH | LOI % |
|---|---|---|---|---|
| 1 | 225 | 3.5 | 5.6 | 8.0 |
| 2 | 200 | 5.0 | 5.8 | 8.0 |
| 3 | 160 | 22.0 | 5.8 | 8.3 |

TABLE VI

| | Sieving Analysis | | | | |
|---|---|---|---|---|---|
| Ex. No. | +40 | 40/60 | 60/80 | 80/100 | −100 |
| 1 | 0.2 | 2.8 | 31.0 | 23.3 | 42.6 |
| 2 | 0.3 | 3.4 | 31.4 | 23.6 | 41.5 |
| 3 | 0.3 | 3.1 | 29.8 | 23.2 | 43.7 |

Tablets were prepared using the formulation and compression equipment described in previous examples. The following results were obtained:

TABLE VII

| Experiment No. | Tablet Weight Variation Coefficient Cv @ 25 kN - % | Hardness (Kiloponds) Average of 20 Tablets |
|---|---|---|
| 1 | 0.2 | 13 |
| 2 | 0.4 | 12 |
| 3 | 0.4 | 14 |

EXAMPLE V

Dicalcium phosphate dihydrate of the type described as DI-TAB® in Example IV was dehydrated using the equipment and dehydration procedures described in Example II.

The product was subjected to three quality control tests, i.e. particle size distribution, L.O.I. at 800° C. and pH for a 20 percent solids slurry. The product of Experiment 2 had a surface area of about 11.6 meters$^2$/gram. The following results were obtained:

TABLE VIII

| Ex. No. | Dehydration Temp. °C. | Time Hr. | pH | LOI % |
|---|---|---|---|---|
| 1 | 120 | 4.0 | 5.8 | 8.4 |
| 2 | 125 | 2.2 | 5.9 | 8.6 |
| 3 | 150 | 1.0 | 5.8 | 8.0 |

TABLE IX

| | Sieving Analysis | | | | |
|---|---|---|---|---|---|
| Ex. No. | +40 | 40/60 | 60/80 | 80/100 | −100 |
| 1 | 0.1 | 3.1 | 32.3 | 23.4 | 41.1 |
| 2 | 0.1 | 2.8 | 30.4 | 23.4 | 43.5 |
| 3 | 0.3 | 2.9 | 31.8 | 23.1 | 42.9 |

Tablets were prepared using the formulation and compression equipment described in previous examples. The following results were obtained:

TABLE X

| Experiment No. | Tablet Weight Variation Coefficient Cv @ 25 kN - % | Hardness (Kiloponds) Average of 20 Tablets |
|---|---|---|
| 1 | 0.2 | 17 |
| 2 | 0.6 | 16 |
| 3 | 0.2 | 15 |

EXAMPLE VI

Dicalcium phosphate dihydrate having a particle size distribution as set forth in TABLE IX was heated in a continuous rotary turbo tray dryer at a feed rate of 68.5 kilograms/hour for 1 hour at a top air temperature of 190° C. and a bottom air temperature of 200° C. until the L.O.I. at 800° C. was reduced to 8.1 percent. The initial and final particle size distributions relative to mesh size are noted in TABLE XI which follows:

TABLE XI

| Through/On | Amount Before Heating | After Heating |
|---|---|---|
| /40 | 0.2 | .3 |
| 40/60 | 0.4 | .6 |
| 60/100 | 60.1 | 59.9 |
| 100/140 | 20.8 | 25.4 |
| 140/200 | 9.7 | 8.2 |
| 200/325 | 7.1 | 4.4 |
| 325/ | 1.6 | 1.2 |

Tablets were prepared by placing the anhydrous dicalcium phosphate (97 percent) and 2 percent Ac-Di-Sol croscarmellose sodium disintegrant in the twin shell V-blender as described in Example I. After mixing for 20 minutes without the intensifier bar, 1 percent magnesium stearate lubricant was added and the mixture was blended for an additional 5 minutes.

Tablets were prepared according to the procedure set forth in Example I with the following results (Compaction Force is in kiloNewtons and Tablet Hardness is in kiloponds and is an average of 10 tablets):

TABLE XII

| Ex. | Compaction Force | Tablet Hardness | Tablet Weight Variation Coefficient |
|---|---|---|---|
| 1 | 10.0 | 4.2 | 0.21 |
| 2 | 13.7 | 6.1 | 0.21 |
| 3 | 17.9 | 9.1 | 0.21 |
| 4 | 22.1 | 11.6 | 0.26 |
| 5 | 25.6 | 14.3 | 0.25 |
| 6 | 29.3 | 16.2 | 0.16 |

Effective tablets are prepared where the average weight variation coefficient is under 0.5. The average thickness variation coefficient for these samples was less than 1.0, the preferred range for that coefficient.

A comparison set of tablets were prepared using DI-TAB ® with the following results:

TABLE XIII

| Ex. | Compaction Force | Tablet Hardness | Tablet Weight Variation Coefficient |
|---|---|---|---|
| 7 | 9.9 | 6.4 | .27 |
| 8 | 13.9 | 9.1 | .15 |
| 9 | 17.7 | 11.7 | .15 |
| 10 | 21.6 | 15.2 | .16 |

TABLE XIII-continued

| Ex. | Compaction Force | Tablet Hardness | Tablet Weight Variation Coefficient |
|---|---|---|---|
| 11 | 25.6 | 16.1 | .21 |
| 12 | 29.8 | 19.0 | .19 |

The average thickness variation coefficient for the samples was less than 1 (the acceptable standard).

EXAMPLE VII

The process of Example VI was repeated using a feed rate of 40.8 pounds/hour, a retention time of 2.5 hours, a top air temperature of 175° C. and a bottom air temperature of 180° C. The product had a particle size distribution of:

TABLE XIV

| On/through | |
|---|---|
| /60 | .6 |
| 60/80 | 14.7 |
| 80/100 | 31.3 |
| 100/140 | 31.6 |
| 140/200 | 14.7 |
| 200/325 | 5.6 |
| 325 | 1.6 |

Tablets prepared with this material according to the procedure of Example VI showed the following results:

| Ex. | Compaction Force | Hardness (Ave. 10 Tablets) | Weight (Ave. 10 Tablets) |
|---|---|---|---|
| 1 | 10.2 | 6.05 | 0.7452 |
| 2 | 13.9 | 9.22 | 0.7447 |
| 3 | 18.7 | 12.53 | 0.7460 |
| 4 | 21.8 | 16.34 | 0.7462 |
| 5 | 26.8 | — | 0.7487 |
| 6 | 30.3 | — | 0.7494 |

EXAMPLE VIII

Six calcium phosphates were analyzed for Radioactive Dentin Abrasivity using calcium pyrophosphate as a reference standard with an assigned RDA value of 100. A slurry of the solids was made from 10 grams per 50 milliliters of 0.5 percent carboxymethylcellulose solution. The following results were obtained:

TABLE XV

| Ex. | Material | Form | RDA (ave.)* | RDA (range) |
|---|---|---|---|---|
| 1 | Anhydrous DCP Prepared in accordance with the Invention | Granular (unmilled) | 49 | 43–66 |
| 2 | Anhydrous DCP Ex. 1 - milled | Powder (−325 mesh) | 47 | 42–54 |
| 3 | Precipitated DCPA | Powder | 271 | 241–285 |
| 4 | DCPD | Granular (unmilled) | 94 | 72–129 |
| 5 | DCPD | Powder | 79 | 70–89 |
| 6 | DCPD | Powder | 60 | 52–70 |

*± 20 percent (estimated)

From this it can be seen that the anhydrous dicalcium phosphate prepared in accordance with the invention as well as its powdered form (Experiments 1 and 2) has significantly less abrasivity than precipitated anhydrous dicalcium phosphate (18 percent of the abrasivity). The anhydrous dicalcium phosphate has almost one/half the abrasivity of its parent unmilled dicalcium phosphate dihydrate represented by Experiment 4.

As used herein, sievings and particle size are based on the U.S. Standard Sieve Series wherein:

| Mesh equals Particle Size in Microns | |
| --- | --- |
| 20 | 840 |
| 40 | 420 |
| 60 | 250 |
| 80 | 177 |
| 100 | 149 |
| 200 | 74 |
| 325 | 44 |

What is claimed is:

1. A granular anhydrous dicalcium phosphate having a Loss on Ignition of about 11 percent by weight or less, a particle size sufficient for direct compression tableting wherein at least 90 percent of the particles are greater than about 44 microns and at least 95 percent of the particles are smaller than about 420 microns and a surface area greater than 5 meters$^2$/gram said granular anhydrous dicalcium phosphate having a Radioactivity Dentin Abrasivity of below about 150.

2. The phosphate as recited in claim 1 wherein at least 80 percent of the particles are greater than 74 microns.

3. The phosphate as recited in claim 1 wherein at least 95 percent of the particles are greater than 44 microns.

4. The phosphate as recited in claim 1 wherein the surface area is greater than about 7 meters$^2$/gram.

5. The phosphate as recited in claim 1 wherein the surface area is greater than about 9 meters$^2$/gram.

6. A process for preparing a directly compressible anhydrous dicalcium phosphate having an L.O.I. of about 11 percent by weight or less, which comprises dehydrating granules of dicalcium phosphate dihydrate of a particle size sufficient for direct compression tableting and sufficiently large to allow dehydration of the granules without forming lumps and without fracturing a majority of the granules, said granules being dehydrated in an amount sufficient to form granular anhydrous dicalcium phosphate wherein at least 90 percent of the granular anhydrous dicalcium phosphate particles are greater than about 44 microns and at least 95 percent of the particles are smaller than about 420 microns said granular anhydrous dicalcium phosphate having a Radioactivity Dentin Abrasivity of below about 150.

7. The process as recited in claim 6 wherein the granules are formed by compaction.

8. The process as recited in claim 6 wherein the granules are formed by dry compacting said dihydrate followed by reducing the compacted material to granular particle size.

9. The process as recited in claim 6 wherein said granules of dicalcium phosphate dihydrate are the unmilled, particle classified, result of the process for manufacturing said dicalcium phosphate dihydrate.

10. The process as recited in claim 6 wherein at least 90 percent of the granules of dicalcium phosphate dihydrate are greater than 44 microns.

11. The process as recited in claim 6 wherein the granules of dicalcium phosphate dihydrate are greater than 44 microns.

12. The process of claim 6 wherein at least 80 percent of the granules of dicalcium phosphate dihydrate are greater than 74 microns.

13. The process as recited in claim 6 wherein the granules are dehydrated sufficient to reduce the Loss on Ignition of the granules to below about 11 percent by weight.

14. The process as recited in claim 6 wherein the granules are dehydrated sufficient to reduce the Loss on Ignition to an amount within the range of from about 8.5 percent to about 6.6 percent by weight.

15. The process as recited in claim 6 which further includes the addition of a pH adjusting agent.

16. The process as recited in claim 6 wherein the surface area is greater than about 5 meters$^2$/gram.

17. The process as recited in claim 6 wherein the surface area is greater than about 7 meters$^2$/gram.

18. The process as recited in claim 6 wherein the surface area is greater than about 9 meters$^2$/gram.

19. The process as recited in claim 15 wherein said agent is tetrasodium pyrophosphate.

20. The process as recited in claim 19 wherein said agent is added to the dicalcium phosphate dihydrate prior to compaction.

21. The product of the process of claim 6.

22. The product of the process of claim 8.

23. The product of the process of claim 9.

24. A process for preparing tablets or dry capsules by direct compression which comprises directly compressing the product of claim 1 into a table form.

25. A process for preparing tablets or dry capsules by direct compression which comprises directly compressing the product of claim 21 into a tablet form.

26. A process for preparing tablets or dry capsules by direct compression which comprises directly compressing the product of claim 22 into a tablet form.

27. A process for preparing tablets or dry capsules by direct compression which comprises directly compressing the product of claim 23 into a tablet form.

* * * * *